(12) United States Patent
Sharkey et al.

(10) Patent No.: US 6,447,508 B1
(45) Date of Patent: Sep. 10, 2002

(54) STENT INDUCTIVE HEATING CATHETER

(76) Inventors: Hugh R. Sharkey, 830 Partridge Ave., Menlo Park, CA (US) 94025; Bruno Strul, 485 Cervantes Rd., Portola Valley, CA (US) 94028

( * ) Notice: Subject to any disclaimer, the term of this patent is extended or adjusted under 35 U.S.C. 154(b) by 89 days.

(21) Appl. No.: 09/595,168

(22) Filed: Jun. 15, 2000

Related U.S. Application Data

(60) Provisional application No. 60/139,546, filed on Jun. 16, 1999.

(51) Int. Cl.[7] ............................................... A61B 18/18
(52) U.S. Cl. ............................ 606/41; 607/98; 607/101; 607/105
(58) Field of Search .............................. 606/32, 39, 40, 606/41, 45, 46, 47, 48, 49, 50, 51, 52; 607/98, 100, 101, 105, 113

(56) References Cited

U.S. PATENT DOCUMENTS

| | | | |
|---|---|---|---|
| 5,454,809 A | | 10/1995 | Janssen |
| 5,749,914 A | | 5/1998 | Janssen |
| 5,972,026 A | * | 10/1999 | Laufer et al. ................. 606/41 |
| 6,197,022 B1 | * | 3/2001 | Baker ........................... 606/33 |
| 6,258,087 B1 | * | 7/2001 | Edwards et al. ............ 600/374 |

* cited by examiner

*Primary Examiner*—Rosiland S. Kearney
(74) *Attorney, Agent, or Firm*—Oppenheimer Wolff & Donnelly LLP; Claude A. S. Hamrick; Justin F. Boyce

(57) ABSTRACT

An electrode catheter assembly for ablation of obstructive material formed within and around a stent inserted within a lumen includes an elongate flexible tube having a distal end and a proximal end, and an electrode assembly attached to the distal end of the tube. The electrode assembly includes: a first electrode formed by a cylindrical body defining a longitudinal axis and having a first end, and an opposite second end, the body having a plurality of slits formed therein, each of the slits extending parallel to the axis from a corresponding first point proximate the first end to a corresponding second point proximate the second end, the slits defining a plurality of elongated deformable segments; and a second electrode disposed along the axis at a distance from the first electrode. A spacer means, disposed between the first and second electrodes, is operative to physically separate and electrically insulate the first electrode from the second electrode. Electrical transmission means provides a first electrical path between a power supply and the first electrode, and a second electrical path between the second electrode and the power supply. Actuator means is provided for moving the first end toward the second end of the body causing the segments to be deformed so that portions thereof are extended radially away from the axis, whereby when the catheter assembly is inserted into a lumen and positioned within an occluded stent, the deformable segments establish an electrically conductive path to the stent.

10 Claims, 3 Drawing Sheets

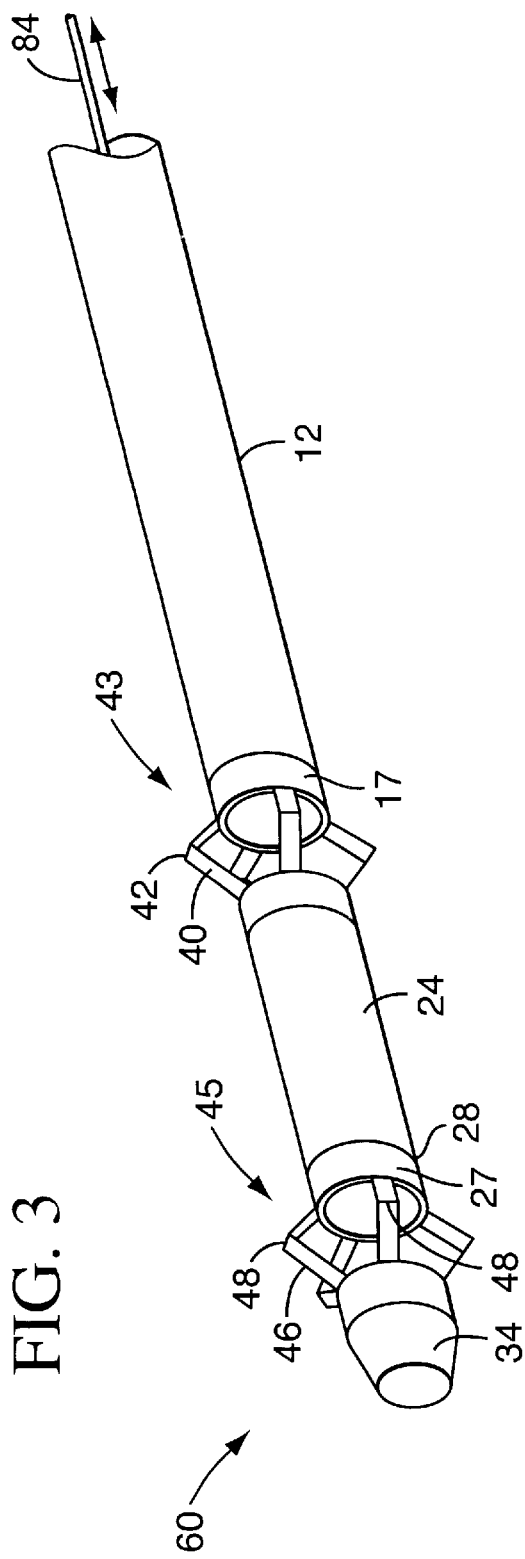
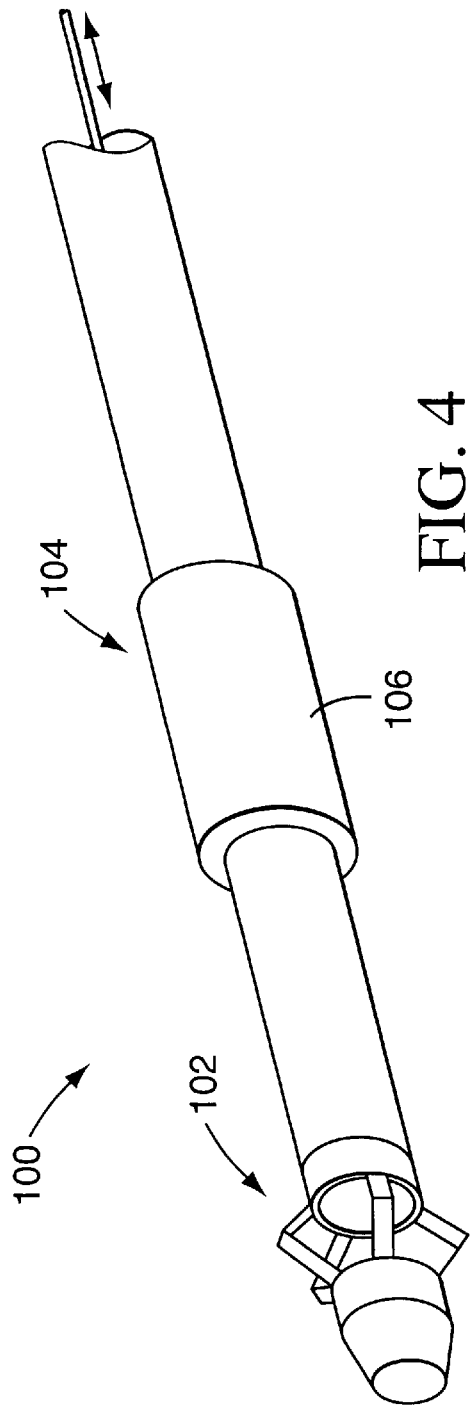
FIG. 3
FIG. 4

STENT INDUCTIVE HEATING CATHETER

CROSS REFERENCE TO RELATED APPLICATIONS

Reference is made to and priority claimed from U.S. Provisional Application Ser. No. 60/139,546, filed Jun. 16, 1999, entitled "Stent Inductive Heating Catheter".

BACKGROUND OF THE INVENTION

1. Field of the Invention

The present invention relates generally to apparatus for removing obstructive material from an occluded lumen of a patient, and more specifically to a catheter mounted electrode device disposable within an occluded stent implanted within a lumen and operative to cause an electrified current to flow through the stent and cause ablation of obstructive material formed in and around the stent.

2. Description of the Prior Art

Obstructive material may be formed in virtually all of the lumens in a body, and may be composed of many different substances. These obstructions may interfere with material transport and fluid flow within the lumen. One example of obstructive material formed within a lumen is atherosclerotic plaque formed within a coronary artery. Other obstructions may occur in any vein or artery such as a coronary, carotid, neurological, peripheral, or renal vein or artery. Additional types of lumens which may be obstructed include bile ducts, all lumens of the genital-urinary tract such as fallopian tubes, and lumens of the gastrointestinal tract such as the intestines or colon. Examples of obstructive material include: all forms of plaque such as fatty plaque, fibrous plaque, and calcific plaque; fibrotic material; mucous; thrombus; and blood clots. The above mentioned lumens and obstructive materials are given as examples only.

A variety of methods and devices have been developed to remove obstructive material from occluded lumens, or to at least alleviate the obstruction. Catheters equipped with cutting blades may be used to slice the obstruction from the lumen. Other methods use heat to resolve obstructive material. It is known that localized heating of a blood vessel wall may prevent the proliferation of smooth muscle cells which are believed to cause restenosis. Laser angioplasty devices generally supply energy to the tip of a catheter to cauterize or burn away obstructions.

Radio frequency (RF) ablation is also known in the prior art for ablating obstructive material formed within a lumen. RF current is directed from an RF power source to an ablating electrode, from which the RF current is provided to the obstructive material. In a monopolar RF ablation device, current return is typically provided via a conductive plate attached to the body of the patient and coupled to the power supply. In a multipolar RF ablation device, more than one electrode is provided at the distal end of the catheter, and the current flows through the obstructive material between at least two of these electrodes. An example of an RF catheter is described in Jannsen (U.S. Pat. No. 5,454,809).

Balloon angioplasty is another common method of removing obstructive material from an occluded lumen. In accordance with balloon angioplasty techniques, a catheter having a deflated balloon is introduced into an occluded lumen and the balloon is inflated. The inflated balloon applies pressure to the obstruction, and to the wall of the lumen. The balloon stretches the lumen, so that fluid flow through the lumen may be improved. However, balloon angioplasty tends to stretch the elastic artery beyond its ability to recoil causing the lumen to contract after the balloon is deflated and withdrawn from the lumen. A well known solution to the problem of lumen contraction is to insert a stent into the lumen.

A stent typically comprises an expandable coil spring or wire-mesh tube. In accordance with a common method for implanting a stent within an occluded lumen, the stent is mounted upon an inflatable balloon catheter. The catheter assembly is then delivered to the occluded area, and the balloon is inflated to radially force the stent into contact with the occlusion. As the stent expands, the lumen of the blood vessel is opened and blood flow is restored. After complete expansion of the stent, the balloon catheter is deflated and removed, leaving the stent behind to buttress and prevent elastic recoil of the blood vessel wall.

While stents have proven effective in preventing lumen restriction, complications often may arise in their use. In particular, obstructions may build up in or through the stent in much the same manner as they would if the stent was not in place, such as by, for example, tissue growth. The stent may irritate the tissue and may allow for thrombin, plaque, or other substances to accumulate on the interior surface of the stent, and on the outer surface of the stent between the stent and the lumen. Such accumulation, referred to as restenosis, may again restrict fluid flow through the lumen, so that efficacy of the stent is reduced or, in severe cases, eliminated. Stent restenosis affects approximately 20% of all stents placed in the coronary vasculature. The problem of restenosis is commonly addressed by attempting to dilate the lumen of the vessel with conventional balloon angioplasty, or by the use of various atherectomy devices. Stent manufacturers have tried to address the problem of restenosis using antifibrogenic coatings, and in some instances with the use of radioactive materials contained within the stent.

Another method for removing obstructive material from within a stent is RF ablation. However, the presence of a stent in an occluded lumen causes some complications for RF ablation because stents are typically formed of conductive material. If an ablating electrode comes into contact with the stent, a short circuit could occur, which may damage the ablation catheter, the stent, or the lumen.

Jannsen (U.S. Pat. No. 5,749,914, filed May 28, 1996, and issued May 12, 1998) discloses an electrosurgical device for ablation of obstructive material within a stent. The device includes a catheter, or elongate flexible tube, having a distal end and a proximal end. One or more ablation electrodes are positioned at the distal end of the catheter, and a power supply is provided in electrical communication with the electrodes. The electrodes are shielded from direct contact with the stent in order to prevent a possible short circuit that may occur if the electrode contacts the stent. The catheter is inserted into the stent, and a first ablation electrode disposed proximate the distal end of the catheter is shielded from physical contact with the stent by a lip of the catheter wall.

Jannsen describes a plurality of circumferentially divided electrodes seated in an annular ridge formed in the exterior wall of the catheter, the electrodes being sized so that they are recessed within the annular ridge. Jannsen also discloses a plurality of ring electrodes disposed along the longitudinal axis of the catheter. A plurality of spacers, projecting radially away from the catheter axis, are disposed between adjacent ones of the ring electrodes. The spacers have a diameter greater than the diameter of the ring electrodes so that the electrodes are prevented from contacting the stent.

According to Jannsen, the stent may conduct current and act as a virtual ground shielding all tissue located exterior to the stent. Jannsen further discloses directly grounding a stent via conducting stylets or probes extending radially from the catheter in order to improve the shielding effect of the stent. A return electrode is provided in electrical communication with the current supply, the return electrode being attachable to a patient. Jannsen discloses a return electrode sized so that it will contact the stent, thereby grounding the stent. This lowers the impedance between the return electrode and the ablating electrodes, and allows for precise ablating of obstructive material between the electrodes and the stent.

As described in Jannsen, it may be inconvenient to have the electrode sized to contact the stent, because the electrode may then interfere with the longitudinal motion of the catheter through the stent. One solution to this problem, as described by Jannsen, is to use an, inflatable balloon located beneath the electrode to selectively increase the diameter of the catheter at the position of the electrode to bring the electrode into contact with the stent. The balloon may be deflated when the catheter is moved through the lumen, and may be inflated when the catheter is in an appropriate position. However, a problem with this method is that using a balloon to extend an electrode radially outward is expensive and awkward. Also, the contact area between the electrode and obstructive material is limited by the shape of electrodes disposed on the balloon. Moreover, the area of contact between the electrode and obstructive material, and ultimately between the electrode and stent, is difficult to optimize using an electrode disposed on an inflatable balloon.

What is needed is a catheter mounted electrode assembly for insertion into a stent to create localized current flow to and through the stent to cause ablation of obstructive material formed within and around the stent.

What is also needed is a multipolar electrode catheter assembly for ablation of obstructive material formed within and around a stent wherein the electrodes are shaped to provide an optimal area of contact between the obstructive material and the electrodes, and ultimately between the electrodes and the stent after obstructive material has been ablated.

Further needed is an electrode catheter assembly for ablation of obstructive material formed within and around a stent wherein the electrodes are shaped so as to precisely control the flow of current between the electrodes and through the obstructive material and the stent in order to maximize efficiency in ablating the obstructive material.

SUMMARY OF THE INVENTION

It is therefore an object of the present invention to provide a catheter assembly having means for creating an electrical current flow through a metallic stent disposed within a lumen to cause ablation of obstructive material formed within and around the stent.

It is also an object of the present invention to provide an electrode catheter assembly for ablation of obstructive material formed within and around a stent wherein the electrodes are shaped to provide an optimal area of contact with the obstructive material and the electrodes, and ultimately between the electrodes and the stent after obstructive material has been ablated.

It is a further object of the present invention to provide an electrode catheter assembly for ablation of obstructive material formed within and around a stent wherein the electrodes are shaped so as to precisely control the flow of current between the electrodes, through the obstructive material, and through the stent in order to maximize efficiency in ablating the obstructive material.

Briefly, a presently preferred embodiment of the present invention includes a catheter assembly for ablation of obstructive material formed within and around a stent inserted within a lumen. The catheter assembly includes an elongate flexible tube having a distal end and a proximal end, and an electrode assembly attached to the distal end of the tube. The electrode assembly includes: a first electrode formed by a substantially cylindrical body defining a longitudinal axis and having a first end, and an opposite second end, the body having a plurality of slits formed therein, each of the slits extending substantially parallel to the axis from a corresponding first point proximate the first end to a corresponding second point proximate the second end, the slits defining a plurality of elongated deformable segments of the body; and a second electrode disposed along the axis at a distance from the first electrode. A spacer means, disposed between the first and second electrodes, is operative to physically separate and electrically insulate the first electrode from the second electrode.

Electrical transmission means is passed through the tube to provide: a first electrical path between a power supply and the first electrode; and a second electrical path between the second electrode and the power supply. Actuator means is provided for moving the first end of the cylindrical body toward the second end of the body causing the segments to be deformed so that portions thereof are extended radially away from the axis, whereby when the catheter assembly is inserted into a lumen and positioned within an occluded stent, the deformable segments establish an electrically conductive path to the stent.

Each of the deformable segments has a corresponding weakened portion formed along a line transverse to the longitudinal axis of the cylindrical body, the segments being deformable about the corresponding weakened portions. The weakened portions of the segments may be formed by perforating, crimping, or bending the segments along the transverse lines.

In an embodiment, the second electrode is also formed by a substantially cylindrical body defining a longitudinal axis and having a first end, and an opposite second end, the body having a plurality of slits formed therein, each of the slits extending substantially parallel to the axis from a corresponding first point proximate the first end to a corresponding second point proximate the second end, the slits defining a plurality of elongated deformable segments of the body.

The actuator means preferably includes: a cable passing through the tube and having a distal end connected to the second end of the cylindrical body, and a proximal end; and retracting means connected to the proximal end of the cable and operative to retract the cable causing the second end to be moved toward the first end of the body.

An important advantage of the present invention is that the deformable segments of the electrodes, which extend radially away from the axis, provide a large surface area for contacting obstructive material formed within a stent implanted within a lumen, thereby allowing for current to be conducted through a large amount of the obstructive material providing efficient ablation of the material. Also, as the obstructive material is ablated by energy provided via the electrodes, the segments of the electrodes may be further extended radially toward the inner wall of the stent, ultimately contacting the inner wall of the stent.

The foregoing and other objects, features, and advantages of the present invention will be apparent from the following detailed description of the preferred embodiment which makes reference to the several figures of the drawing.

IN THE DRAWINGS

Figure 1:
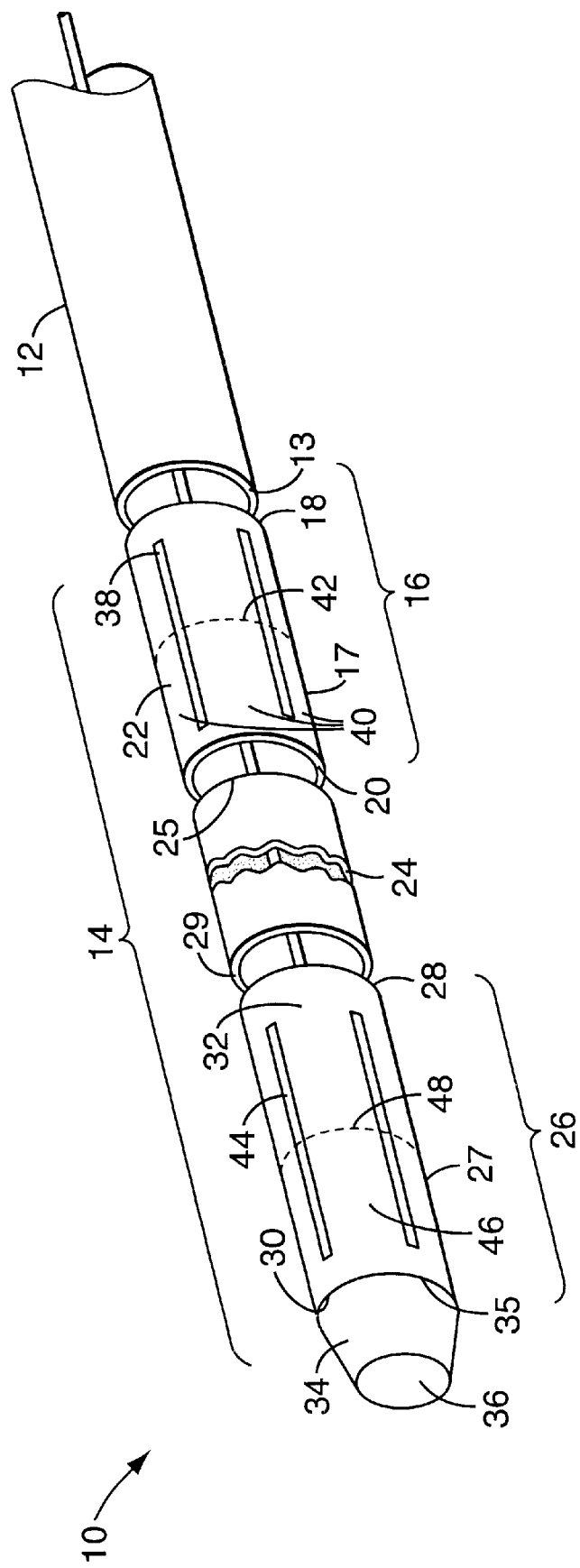
FIG. 1 is an exploded perspective view of a multipolar electrode catheter assembly in accordance with the present invention, the assembly including a pair of radially deployable/retractable electrodes shown in a retracted position.

FIG. 3 is a perspective view of the electrode assembly of FIG. 1 showing the electrodes deployed to extend radially away from the longitudinal axis of the catheter assembly; and FIG. 4 is a perspective view of an alternative embodiment of the electrode assembly of the present invention having a first deployable/retractable electrode, and a second non-deployable/retractable electrode that is generally cylindrical in shape.

DETAILED DESCRIPTION OF THE PREFERRED EMBODIMENTS

FIG. 1 shows at 10 an exploded perspective view of a multipolar electrode catheter assembly in accordance with the present invention, the assembly 10 including: a catheter 12 having a proximal end (not shown) and a distal end 13; and an electrode assembly 14 adapted for attachment to the distal end of the catheter as further explained below. Although shown exploded, various components of the catheter assembly 10 shown and unshown in this Figure are described below as they are assembled in accordance with an embodiment of the present invention. The electrode assembly 14 is constructed of an appropriate length and diameter, and of appropriate materials so that it may be inserted within an occluded stent (not shown) implanted within a lumen, as further explained below.

The electrode assembly 14 includes: a first electrode 16 formed by a first cylindrical body 17 having a first end 18 attached to the distal end 13 of the catheter 12, and a second end 20; an insulating cylindrical spacer 24 formed of a length of tubular electrically insulating material (e.g., Teflon), and having a first end 25 attached to the second end 20 of the cylindrical body 17, and a second end 29; a second electrode 26 formed by a second cylindrical body 27 having a first end 28 attached to the second end 29 of the spacer 24, the electrode 26 also having a second end 30; and an end unit 34 attached to the second end 30 of cylindrical body 27. In the preferred embodiment, the end unit 34 is substantially frustoconically shaped. In alternative embodiments, the end unit 34 might be dome-shaped, conical, or of any other shape suited for insertion into the lumen of a vein, artery or other tubular structure of a patient.

In the preferred embodiment, the first and second cylindrical bodies 17 and 27, and the end unit 34 are all formed of conductive material, and the end unit 34 is electrically coupled to the second cylindrical body 27 but may have differing outer diameters. The illustrated cylindrical bodies, spacer, and end unit have substantially equal outer diameters, but may have differing outer diameters. The first and second cylindrical bodies may be threadably attached to the spacer 24 or attached by other means such as epoxy. In an alternative embodiment, the end unit 34, body 27, spacer 24, and body 17 may all be formed as an integral unit.

The first cylindrical body 17 has a plurality of longitudinally extending slits 38 formed through its wall 22; each of the slits 38 extending along a substantial portion of the length of the body. The slits 38 define a plurality of elongated deformable, distortable or articulatable segments 40, each having a weakened portion formed along a waist line 42 lying in a plane transverse to the longitudinal axis of the electrode assembly. Each of the segments 40 is thus plastically deformable about its waist portion so that each segment may be bowed outwardly to form a radially extending electrode. In the preferred embodiment, the waist portions of the segments 40 may be weakened by perforating, crimping, or bending the segments along the transverse lines 42 to enhance the flexibility thereof. In the depicted example, the body 17 includes four of the slits 38 formed therein defining four segments 40. In alternative embodiments, the first cylindrical body may include any other number of slits formed therein to define a corresponding number of deformable segments. The four slits 38 have substantially equal lengths, and are spaced at substantially equal circumferential distances from each other, but alternatively could be spaced differently to yield segments of differing widths.

The second cylindrical body 27 likewise includes a plurality of slits 44 formed through its wall 32 and extending substantially parallel to the longitudinal axis of the electrode assembly. The slits 44 also define a second plurality of elongated deformable, distortable or articulatable segments 46. Each segment 46 also has a corresponding portion of enhanced flexibility formed along a second waist line 48 which is transverse to the longitudinal axis of the electrode assembly. As in the other body 17, the flexibility of the segments is enhanced by perforating, crimping, thinning or bending the segments along the waist line 48. In the depicted embodiment, the second cylindrical body 27 also includes four slits 44 formed therein to define four deformable segments 48. Alternatively, the second cylindrical body may include any other number of slits formed therein to define a corresponding number of deformable and articulatable segments. The four slits 44 are of substantially equal length, and are spaced at substantially equal circumferential distances from each other. Note that the slits 38 and 44 could be of any suitable configuration and need not be straight lines or even be parallel to each other. For example, the slits might be diamond shaped so that the segment width at the waist line is less than the width at either end.

Figure 2:
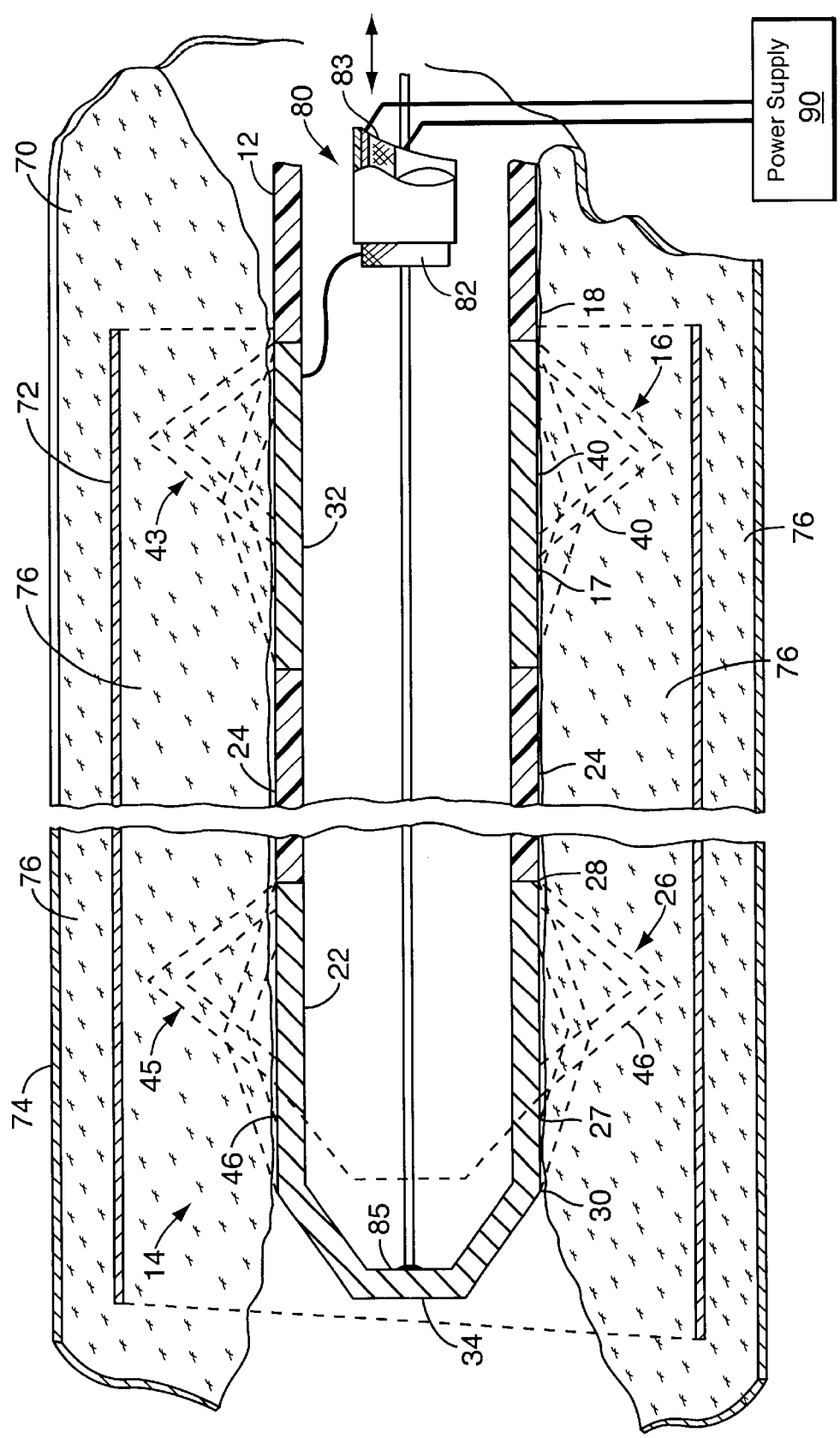
FIG. 2 is an axial cross sectional view taken along the longitudinal axis of the electrode assembly of FIG. 1 and shown inserted into an occluded stent implanted within a lumen.

FIG. 2 shows an axial sectional view illustrating at 70 the electrode assembly 14 inserted into the interior of an occluded stent 72 which is implanted within a lumen 74. Collagenous obstructive material 76 is shown disposed between the stent 72 and the electrode assembly 14, and also between the stent and the lumen 74. The obstructive material 76 restricts the effective diameter of the lumen 74 in which the stent is implanted, and therefore interferes with flow of fluid (or other substance) therethrough. The stent 72 is preferably formed of electrically conductive material, although an occluded stent formed using other materials may also be cleared using the present invention but with less facility.

In the depicted embodiment, the catheter assembly 10 further includes a modified coaxial conductor means 80 including a slidable (retractable/extendible) electrically conductive cable or rod 84, the distal end of which is attached to end cap 34 at 85, and an outer conductor 82 perhaps formed by electrically conductive wire mesh wrapped about a tubular core of insulation material that electrically insulates the outer conductor 82 from the conductive cable 84. The end cap 34 is electrically conductive and is ohmically connected to the cylinder 40. Thus, electrical current flowing through cable 84 will be communicated to the deployable electrode elements 40 and 46.

The coaxial means 80 provides an electrical transmission path between a power supply 90 and the first and second electrode elements 40 and 46. In the preferred embodiment, the power supply 90 is a radio frequency (RF) signal generator. The inner conductor 84 also serves as a retraction/extension cable which when pulled by an actuator means (not shown) collapses the second end 30 of the body 27 towards the first end 28 so that the segments 46 are deformed outwardly and articulated, as shown by the dashed lines, to form the forward stent contacting electrode elements 45. Further retraction of cable 84 by the actuator means causes the second end 20 of body 17 to be forced towards the first end 18 so that the segments 40 deform outwardly to form the aft stent contacting electrode elements 43. Conversely, extension of cable 84 serves to elongate the electrode segments causing them to radially retract so that the catheter can be withdrawn from the lumen.

As mentioned above, the thickness of the cylinder walls 22 and 32 of the cylindrical bodies 17 and 27 may be varied in order to vary the amount of force required to collapse the slotted cylinders and deploy the deformable electrode elements. The amount of force required to collapse the cylindrical bodies may also be varied by varying the extent to which the corresponding articulatable segments 40 and 46 are dimensioned, perforated, crimped, or bent in their midsections. Alternatively, two separate electrical conductors that are coaxial, or otherwise configured, can be imbedded in the catheter structure and extended to make contacting connections with the respective electrodes. In this case, the actuating element might be a flexible, but rather stiff, metal or plastic rod extending through the catheter and being suitably attached to one or both of the electrodes for causing deployment and retraction thereof.

In FIG. 3 a perspective view illustrates the electrode assembly 10 after the cable 84 has been retracted and the segments 40 and 46 have been deformed outwardly, or articulated, so that medial portions of the segments 40 and 46 are extended radially away from the catheter axis to form the electrodes 45 and 43. The segments 46 of the second cylindrical body 27 are deformed as the second end 30 of the body 27 is pulled toward the first end 28 in further response to the retraction of cable 84 (FIG. 2). The segments 40 of the first cylindrical body 17 are likewise deformed, or articulated, as the second end 20 of the body is moved toward the first end 18 in response to the same retractive force.

The apparatus may be designed so that the length of the electrode assembly 14 (FIG. 1) is initially slightly longer than the stent 72 so that when the electrodes are deployed, they contact opposite end portions of the stent. Positioning of the electrode assembly 14 within the stent may be determined in accordance with a variety of techniques. The catheter assembly may include optical means for allowing visual positioning and even inspection of the interior of the lumen 74 in which the stent is inserted. Visualization techniques may be used to determine the location of the assembly 14 within the stent, the location of the stent 72, and the composition and configuration of the obstructive material 74.

Other locating means (not shown) may also be included at the distal end of the catheter, so that an operator of the catheter assembly 10 may determine the location of the electrode, assembly 14 in relation to the stent 72. Such means may include ultrasound transducers that are coupled to suitable ultrasound processors. Other means such as, for example, fiber optics coupled to optical sensors, or electrical impedance sensing means, may also be used. The locating means may also provide information as to the amount of obstructive material, the physical configuration and location, and the type of occluding material that may be within the stent. The electrode assembly may also be positioned using x-ray, ultrasonic, fluoroscopic or other means.

The locating means may also include means for sensing other parameters of the stent, obstructive material, or lumen and such means may be used in conjunction with the ablation of the obstructive material, so that after the material is reduced, an inspection may again be performed, the electrode assembly 14 positioned to a new location, and the ablation process repeated.

In another alternative configuration, the stent itself may be marked with radiopaque, markers and be visualized using fluoroscopy techniques. Such markings, if present, may be used in conjunction with the catheter positioning means to determine the position of the electrodes within the stent. If the stent is made of material which renders it highly radiopaque and makes it difficult to quantify flow or luminal opening within the framework of the stent by conventional dye injection, a combined imaging/visualization technique may be used.

Positioning of the ablating electrode assembly may be further aided by sensing the impedance between the electrodes 16 and 26. The impedance will vary depending on whether the electrodes 43 and 45 are within or not within the stent 72 because the stent is, in general, conductive and provides a change in electrical properties and propagation. By successively sensing impedance between the electrodes with relatively low applied energy, and moving the catheter 10, the electrode assembly may be positioned as desired within the stent before ablating energy is supplied.

Once the electrode assembly is properly positioned within the stent, ablation of the obstructive material may be commenced. As RF energy is applied to the electrodes, portions of the obstructive material immediately adjacent the first and second electrodes are heated by molecular friction generated by energy passing through the material. Additionally, the metal component of the stent is inductively coupled to store electromagnetic energy, thereby producing a secondary source of heat to the portions of the obstructive material immediately adjacent the stent. When the electrode assembly is properly positioned within the stent, current supplied from the power supply via the electrodes also flows through the obstructive material and the stent. The current flows substantially within the body of the stent if, as is usually the case, the conductive material of the stent has a lower resistivity then the resistivity of the obstructive material.

The material contained within the inner diameter of the stent is thus heated both centrally by RF radiation from the electrodes, and is also heated at the surface of the stent, thereby efficiently reducing the obstructive material.

Ideally, the first electrode assembly 14 is positioned so that the first set of deployed segments of the first electrode 43 will make contact with the most distal portion of the interior surface of the stent 72, and the second set of segments of the second electrode 45 will make contact with the most proximal portion of the interior surface of the stent. In practical terms, spacing of the electrodes may only cover some portion of the entire length of the stent.

FIG. 4 is a perspective view showing at 100 an alternative embodiment of the electrode assembly of the present invention including a first extendible/retractable electrode 102, substantially identical to the electrode 45 (FIG. 1), and having articulatable segments; and a second non-extendible, non-retractable electrode 104 formed by a cylindrical member 106. The second electrode 104 does not include articulatable segments. In operation, upon positioning of the assembly 100 into a stent, energizing the assembly, the second electrode 104 provides a return path for current flowing from electrode 102 through the stent and obstructive material at the proximal end of the stent.

Although the present invention has been particularly shown and described above with reference to a specific embodiment, it is anticipated that alterations and modifications thereof will no doubt become apparent to those skilled in the art. It is therefore intended that the following claims be interpreted as covering all such alterations and modifications as fall within the true spirit and scope of the invention.

What is claimed is:

1. An electrode catheter assembly for ablation of obstructive material formed within and around a stent inserted within a lumen, said catheter assembly comprising:

an elongated flexible tube having a distal end and a proximal end;

an electrode assembly attached to said distal end of said tube and defining a longitudinal axis, said electrode assembly including, a first electrode having a plurality of first deformable electrically conductive segments capable of being extended radially away from said axis and retracted back toward said axis, said first electrode being formed by a first conductive and substantially cylindrical body having a first end and a second end, said first body having a plurality of first slits formed therein extending in parallel from points proximate said first end to points proximate said second end, said first slits defining said plurality of first conductive segments;

a second electrode disposed along said axis at a distance from said first electrode, and having a plurality of second deformable electrically conductive segments capable of being extended radially away from said axis and retracted back toward said axis, said second electrode being formed by a second conductive and substantially cylindrical body having a third end and a fourth end, said second body having a plurality of second slits formed therein extending in parallel from points proximate said third end to points proximate said fourth end, said second slits defining said plurality of second conductive segments; and spacer means having a predetermined fixed length coaxially aligned with and disposed between said first and second electrodes and operative to physically separate and electrically isolate said first electrode from said second electrode;

electrical transmission means passing through said tube and said electrode assembly and providing a first electrical path between a power supply and said first electrode, and providing a second electrical path between said second electrode and the power supply; and actuator means for causing said first and second deformable segments to be selectively extended radially away from said axis, and retracted radially toward said axis, said actuator means including a cable passing through said tube and said electrode assembly and having a distal end connected to the distal end of said electrode assembly, and a proximal end connected to a means accessible to a user;

whereby when said electrode assembly is inserted into a lumen and positioned within an occluded stent, said actuator means can be used to draw the distal end of said electrode assembly toward the distal end of said tube and thereby extend said first and second deformable segments outwardly to establish an electrically conductive path from said first segments to and through said stent and the obstructive material for return to said second segments thereby ablating the obstructive material.

2. An electrode catheter assembly as recited in claim 1 wherein each of said deformable segments has a corresponding weakened portion formed along a waist line transverse to said longitudinal axis, said segments being deformable about said corresponding weakened portions.

3. An electrode catheter assembly as recited in claim 2 wherein said weakened portions of said segments are formed by perforating said segments along said waist lines.

4. An electrode catheter assembly as recited in claim 2 wherein said weakened portions of said segments are formed by crimping said segments along said waist lines.

5. An electrode catheter assembly as recited in claim 2 wherein said weakend portions of said segments are formed by thinning said segments along said waste lines.

6. An electrode catheter assembly as recited in claim 2 wherein the weakened portions of said first segments are stronger than the weakened portions of said second segments so that said actuator means causes said second segments to be deformed outwardly at substantially the same time that said first segments are deformed outwardly as the distal end of said electrode assembly is drawn toward the distal end of said tube.

7. An electrode catheter assembly as recited in claim 1 wherein said cable is of conductive material, and provides said first electrical path.

8. An electrode catheter assembly as recited in claim 1 wherein said spacer is formed by a substantially cylindrical spacer body made of electrically non-conducting insulating material having a length selected so that the axial distance between the extended first and second segments bears a predetermined relationship to the length of the stent.

9. An electrode catheter assembly as recited in claim 1 wherein the power supply is a radio frequency power supply.

10. An electrode catheter assembly as recited in claim 1 wherein the power supply is a microwave power supply.

* * * * *